United States Patent [19]

Hudson

[11] Patent Number: 4,888,385

[45] Date of Patent: Dec. 19, 1989

[54] BOP REAGENT FOR SOLID PHASE PEPTIDE SYNTHESIS

[75] Inventor: Derek Hudson, San Anselmo, Calif.

[73] Assignee: Millipore Corporation, Bedford, Mass.

[21] Appl. No.: 44,185

[22] Filed: Apr. 30, 1987

[51] Int. Cl.[4] .................... A61K 37/43; C07K 7/10
[52] U.S. Cl. ............................... 525/54.11; 530/333; 530/334
[58] Field of Search ................ 525/54.11; 530/333, 530/334

[56] References Cited

U.S. PATENT DOCUMENTS 4,581,168  4/1986  Diaz et al. ........................ 530/324
4,636,490  1/1987  Martinez et al. .................. 514/15

*Primary Examiner*—John Kight
*Assistant Examiner*—Nathan M. Nutter
*Attorney, Agent, or Firm*—Andrew T. Karnakis; Paul J. Cook

[57] ABSTRACT

A novel method of activation of a protected amino acid using Benzotriazolyloxytris(dimethylamino)phosphonium Hexafluorophosphate (BOP) as an activator for solid phase peptide synthesis is provided. Hydroxybenzotriazole is included in preferred embodiments. An intermediate acyloxyphosphonium salt is formed from the protected amino acid and the BOP which immediately reacts with HOBt to form an ester without formation of the less reactive symmetrical anhydride. A tertiary or quaternary substituted nitrogen compound must be used to produce a carboxylate of the protected amino acids as it also functions to increase their solubility.

16 Claims, 3 Drawing Sheets

BOP REAGENT FOR SOLID PHASE PEPTIDE SYNTHESIS

BACKGROUND OF THE INVENTION

This invention relates to improved methods of activation for solid phase peptide synthesis and more particularly to the use of Benzotriazolyloxytris(dimethylamino)phosphonium Hexafluorophosphate (BOP) Reagent and BOP in combination with hydroxybenzotriazole (HOBt) Modified Reagents.

Solid phase peptide synthesis typically begins with covalent attachment of the carboxyl end of a first alpha-amino protected acid through an organic linker to an insoluble synthesis resin bead. This can be illustrated as:

wherein (P) is the insoluble synthesis resin, $Aa_1$ is the first amino acid and X is a protecting group such as Fmoc, t-Boc and the like.

The general synthesis cycle then consists of deprotection of the alpha-amine group of the last amino acid, washing and, if necessary, neutralization, followed by reaction with a carboxyl activated form of the next alpha-amine protected amino acid to be added. The peptide chain then becomes:

wherein $Aa_2$ is the second amino acid. The cycle is repeated to the $n^{th}$ amino acid to yield:

wherein $Aa_n$ is the $n^{th}$ amino acid.

Following the synthesis of the entire peptide chain in the desired sequence, the organic link of the peptide chain to the resin bead is cleaved and the dissolved peptide is separated from the insoluble resin and purified.

Although the process is simple in principle, it is difficult to obtain peptides having over 30 amino acids with any substantial purity. This is due to the fact that the average step yield has a profound effect on the purity of the peptide product, as illustrated by the values in the following table for synthesis of a 30 amino acid peptide.

TABLE I

| 30 AMINO ACID PEPTIDE | |
| --- | --- |
| Step Yield | Purity |
| 95.0% | 21% |
| 99.5% | 86% |
| 99.7% | 91% |

The results are even more problematic for longer peptides. A peptide with 101 residues and a step yield of 99.0% provides a product of only 36% purity. In all cases, the by-products of the peptide synthesis are a complex mixture of molecules that are chemically similar to the peptide product. Chromatographic purification is difficult and time consuming because the relative amount of by-product molecules often exceeds about 25%.

The efficiency of the step yield can be judged by the purity of the synthesized peptide and is dependent on many factors including the nature and quality of the protected amino acids, solvent purity, chemical integrity of the resin, the chemical nature of the organic linker, the form of the activated carboxyl of the amino acid, efficiency of the wash steps, the synthesis protocol, and in some instances, the identity of an amino acid in conjunction with a particular sequence segment to which it is being added. Each of these factors is significant in each coupling step.

The automated prior art coupling processes available use diisopropylcarbodiimide (DIPCDI) or dicyclohexylcarbodiimide (DCCI) as activators for addition of the next protected amino acid residue in the sequence. These activators which form symmetrical anhydride or other active intermediates work poorly in polar solvents, such as dimethylformamide. However, such solvating solvents are essential in the synthesis of large peptides because of their ability to prevent aggregation of peptide chains, and increase coupling yields.

Accordingly, it is desirable to provide an improved activation method for solid phase peptide synthesis which increases coupling efficiency and overcomes the problems associated with prior art procedures.

SUMMARY OF THE INVENTION

Generally speaking, in accordance with the invention a novel method of activation of a protected amino acid using BOP Reagent as an activator for solid phase peptide synthesis is provided. A preferred activator is a modified BOP Reagent including an equivalent amount of HOBt. The coupling mechanism includes formation of an intermediate acyloxyphosphonium salt formed from the protected amino acid and the BOP. The salt immediately reacts with the HOBt to form an ester without formation of the less reactive symmetrical anhydride. A tertiary or quaternary substituted nitrogen compound must be used to form a carboxylate salt of the protected amino acids and to increase solubility in desirable solvents, such as DMF.

Accordingly, it is an object of the invention to provide an improved method of activation of protected amino acids for solid phase peptide synthesis.

Another object of the invention is to provide a method using BOP Reagent as an activator in solid phase peptide synthesis.

A further object of the invention is to provide an improved solid phase peptide synthesis activator including BOP-HOBt Reagent.

Still another object of the invention is to provide a method of solid phase peptide synthesis wherein a hydroxybenzotriazole active ester intermediate is formed without formation of a symmetrical anhydride.

Still a further object of the invention is to provide an efficient method of solid phase peptide synthesis that produces high purity peptide yields.

Still other objects and advantages of the invention will in part be obvious and will in part be apparent from the specification.

The invention accordingly comprises the several steps and the relation of one or more of such steps with respect to each of the others, and the composition possessing the features, properties, and the relation of constituents, which are exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which.

DESCRIPTION OF THE PREFERRED EMBODIMENTS

The BOP Reagent and modified BOP-HOBt Reagent utilized in solid phase peptide synthesis in accordance with the invention may be utilized with any conventionally protected amino acids. Such alpha amine protecting groups include t-Boc, Fmoc, Bpoc, Dts and the like. The most widely used protecting groups are t-Boc and Fmoc. These methods preform a protected acyloxyphosphonium salt which then forms a symmetrical acid anhydride. The addition of Hydroxybenzotriazole results information of an intermediate hydroxybenzotriazolyl active ester which couples with the reactive functionality on the solid support or the unprotected amino acid on the growing peptide chain.

Figure 1:
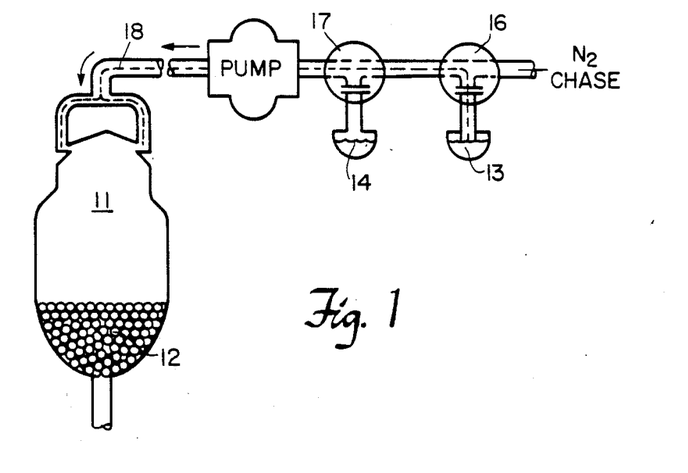
FIG. 1 is a diagrammatic illustration showing an apparatus for performing automated solid phase peptide synthesis suitable for use in accordance with the invention.

FIG. 1 is a diagrammatic representation of a peptide synthesis apparatus suitable for automated computer controlled solid phase synthesis. Such apparatus are available from Biosearch, Inc. of San Rafael, Calif.

Present automatic peptide synthesizers conventionally involves preactivation of a protected amino acid utilizing Diisopropylcarbodiimide (DIPCDI). The synthesis is carried out in a reaction vessel 11 which includes a synthesis resin 12 therein. Reaction vessel 11 is coupled to a source of protected amino acid 13 and a source of DIPCDI activator 14, in a solvent such as $CH_2Cl_2$. Protected amino acid from amino acid reservoir 13 is fed to reaction vessel 11 through a line 18 by an amino acid control valve 16 and DIPCDI activator is fed into line 18 and mixed with the amino acid by an activator valve 17. Amino and valve 16 and activator valve 17 are activated in brief alternate intervals so that protected amino acid and DIPCDI activator are mixed in line 18 for a preselected time prior to being fed into reaction vessel 11.

After the coupling reaction under a nitrogen atmosphere in reaction vessel 12 is complete, the protected amino acid now coupled through its carboxylic acid group to synthesis resin 12 is deblocked with, for example trifluoroamine (TFA), washed with a base and the next activated amino acid residue is added to reaction vessel 11. Upon obtaining the desired peptide residue, the peptide is cleaved from synthesis support 12, generally with hydrofluoric acid (HF). This protocol when the amino acid is protected with t-Boc may be illustrated by the following:

-continued

When the amino acid is protected with Fmoc damage to the peptide product caused by the final harsh hydrofluoric acid cleavage step may be avoided. The Fmoc protecting group can be cleaved from the synthesis resin by TFA in $CH_2Cl_2$. The protocol for the Fmoc protected amino acids is as follows:

These conventional solid state syntheses utilizing DIPCDI activation may also include active ester formation with Hydroxybenzotriazole (HOBt) and symmetric anhydride activation. In both the t-Boc and Fmoc protocols a wide variety of synthesis resins, such as polystyrene, polystyrene cross-linked with divinyl benzene and polyacrylamide resins may be utilized. The synthesis resin is generally in the form of porous beads.

Figure 2:
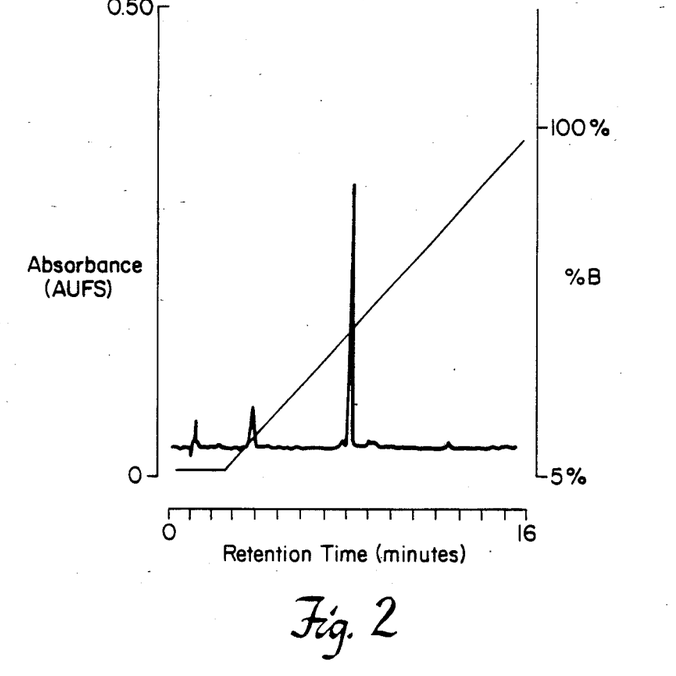
FIG. 2 is an HPLC (high pressure liquid chromotography) profile of an acyl carrier protein (ACP 65-74) synthesized using Fmoc protected amino acids activated by a DIPCDI activation agent.

The HPLC profile of a product direct from cleavage of the 10 reside sequence 65-74 of acyl carrier protein synthesized on a Biosearch MODEL 9500 Peptide Synthesizer in accordance with Fmoc protected acids is shown in FIG. 2. The product was synthesized on a functionalized amino polystyrene resin with mixing of the Fmoc protected amino acids and DIPCDI activator in the synthesizer as illustrated diagrammatically in FIG. 1.

The ACP 65-74 sequence is:

and was analyzed under the following conditions:
Column: Vydac C18 (218TP 546), 5M 4.6 mm I.D.×250 mm L
Gradient: 5% B for 3 min., 5% to 100% B in 17 min.
Solvent A: 0.05% TFA in H$_2$O
Solvent B: 0.05% TFA in ACN
Temperature: Ambient
Detector: UV at 230 nm, 0.5 AUFS The preparation of BOP Reagent utilized in peptide coupling in accordance with the invention is described by J. R. Dormoy and B. Castro in Tetahedron Letters, 35, pp. 3321-3323 (1979). Hexamethyl phosphoric triamide (HMPT) is reacted with phosphochloride at room temperature according to the following scheme:

Y = N(CH$_3$)$_2$

B = N—benzotriazolyl

The protected amino acids utilized with the BOP Reagent in accordance with the invention are dissolved in an organic solvent and converted to a carboxylate form prior to coupling. The organic solvent may be any non-nucleophilic organic solvent, such as dimethylformamide (DMF), methylene chloride (CH$_2$Cl$_2$) and the like. In order to produce the carboxylate salt and to improve solubility of the protected amino acids, an organic base is added to the amino acid in an organic solvent. The base may be a tertiary or quaternary ammonium compound such as N-Methylmorpholine, triethylamine, tri(isopropyl) amine and the like.

The BOP Reagent is utilized in the coupling in an amount between about 0.5 to 2.0 equivalents of BOP per equivalent of protected amino acid. Preferably, the BOP Reagent is present in an amount between about 1.0 to 1.5 equivalents per equivalent of amino acid.

When the Hydroxybenzotriazole (HOBt) is utilized in the modified BOP-HOBt Reagent, there is little reason to use less than about one equivalent per equivalent of acid and usually between 1.0 to 2.0 equivalents of HOBt per equivalent of amino acid is used. Preferably, between about 1.0 and 1.5 equivalents of HOBt per equivalent of amino acid is utilized.

The base to ionize the amino acid carboxyl group such as N-Methylmorpholine, is present in an amount of not less than about 1.0 equivalents to 2.0 equivalents per equivalent of amino acid. The amount of base should not exceed about 2.0 equivalents in order to avoid racemization. Preferably, between about 1.0 and 1.5 equivalents of base per equivalent of amino acid is utilized.

In the following examples, each synthesis is performed on a Biosearch MODEL 9600 Peptide Synthesizer. In each case, the amino acid couplings are preformed at room temperature in the MODEL 9600 Peptide Synthesizer under a nitrogen atmosphere with dissolution of the Fmoc amino acid and its activation by the BOP reagent occurring in each of 20 amino acid reservoirs. Such a method of operation is ideally suited to a peptide synthesizer in which the amino acids are stored as dry powders in capsules. The following Examples are set forth by way of illustration only, and not intended in a limiting sense.

EXAMPLE 1

An ACP 65-74 sequence wherein t-Boc protected amino acids were activated with BOP Reagents in accordance with the invention was prepared with a flow through column reaction system. For each acid the coupling time was about one hour at room temperature. A typical coupling for tyrosine (Tyr) in the peptide product was as follows. t-Boc-Tyr(Bzl)-OH (74.2 mg. 0.2 mmol), BOP Reagent (88.4 mg, 0.2 mmol) and 1 ml of 0.2M N-Methylmorpholine (NMM) in Dimethylformamide (DMF) were mixed for one minute and added to the reactor vessel for coupling. Complete Solvent B: 0.05% TFA in ACN
Temperature: Ambient
Detector: UV at 230 nm, 0.5 AUFS
The amino acid analysis is as follows:

| Asx | 2.00 | Gln | 1.00 |
|-----|------|-----|------|
| Gly | 1.07 | Ala | 2.04 |
| Val | 0.93 | Lle | 1.92 |
| Tyr | 1.02 | | |

It is believed that the reaction mechanism for the BOP Reagent activated coupling in accordance with the invention is as follows:

coupling took place within 1 to 2 minutes.

EXAMPLE 2

The ACP 65-74 sequence of Example 1 was prepared using BOP Reagent and one equivalent of HOBt (31 mg, 0.2 mmol) added, dissolved and activated by the addition of 1 ml 0.3M NMM. Again, complete coupling took place within one to two minutes after adding the modified BOP-HOBt Reagent and protected amino acid to the reaction vessel.

Preactivation times can vary as desired. The minimum time required is something less than about one minute, but may be as long as ten minutes.

EXAMPLE 3

An ACP 65-74 peptide sequence was prepared using solid Fmoc amino acids with the MODEL 9600 peptide synthesizer. The Fmoc amino acids and BOP reagent were placed in 9 separate reservoirs and 5 ml 0.3M NMM in DMF was added and mixed for about ten minutes. All the Fmoc amino acids rapidly and completely solubilized. The sequence was prepared following the protocol described in Example 1.

Figure 3:
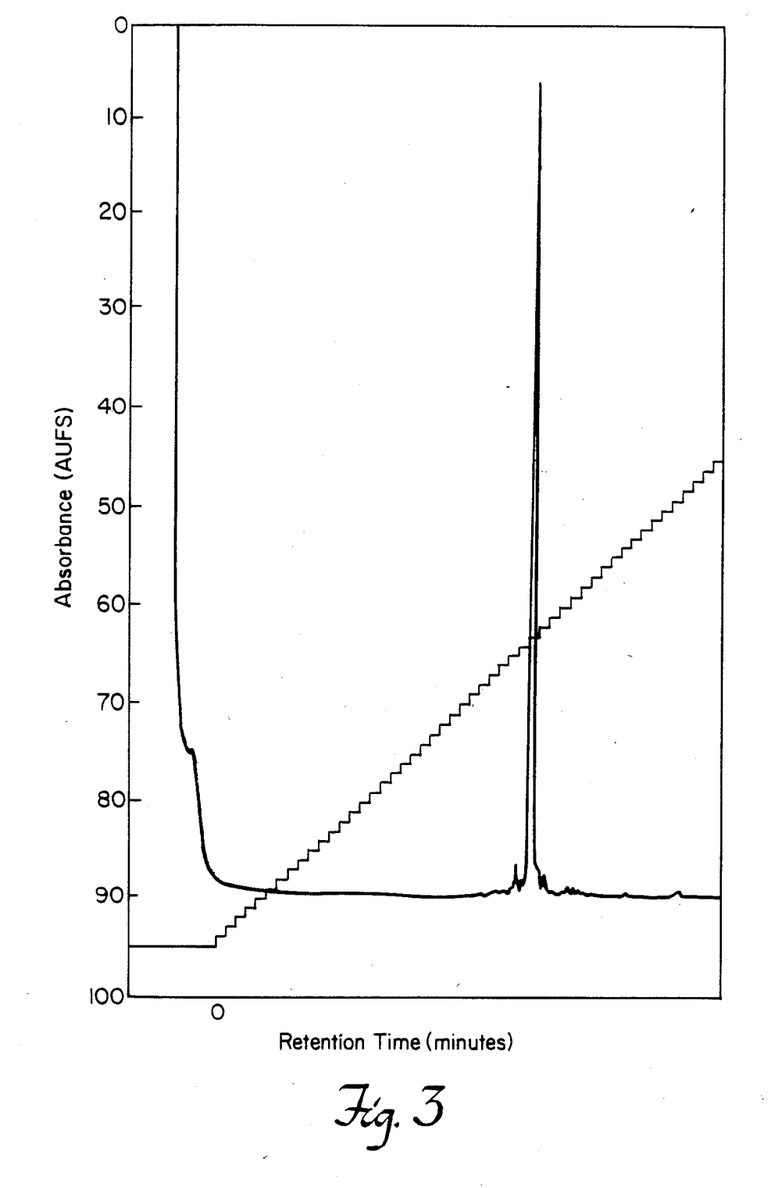
FIG. 3 is an HPLC profile of an ACP 65-74 protein synthesized in accordance with the invention.

The HPLC for the ACP 65-74 sequence product is shown in FIG. 3. The HPLC conditions were as follows:
Column: Vydac C18 (218TP 546), 5M 4.6 mm I.D.×250 mm L
Gradient: 5% B for 3 min., 5% to 100% B in 17 min.
Solvent A: 0.05% TFA in H$_2$O

EXAMPLE 4

Competition experiments demonstrate that under the reaction conditions followed the BOP Reagent functions to form the symmetrical acid anhydride within about one minute. During the remaining ten minutes of preactivation mixing a portion of the symmetrical anhydride is converted by HOBt liberated from the BOP Reagent to form an intermediate hydroxybenzotriazole active ester. This active ester intermediate then couples with the available reactive functionalities on the synthesis resin or the coupled amino acid in the peptide chain.

Use of the BOP Reagent in solid phase peptide synthesis has been found to provide greater coupling efficiency than obtained utilizing preformed symmetrical anhydrides. Surprisingly, when one equivalent of BOP and one equivalent of HOBt in the presence of an effective amount of N-methylmorpholine is used a coupling efficiency almost twice that of the corresponding preformed symmetric anhydride results. This is believed to be due to formation of the intermediate acylphosphonium salt which then reacts immediately with the additional HOBt present in the modified BOP-HOBt Reagent to form the HOBt ester before there is an opportunity to form the less reactive symmetrical anhydride. It is anticipated that the coupling with BOP Reagent may eliminate dehydration side reactions of asparagine and glutamine which occur when coupling with the symmetric anhydrides.

The results from the comparison of the BOP Reagent and the symmetrical anhydrides are set forth in TABLE II:

| Run Code | Set | Comp 1 | Fmoc:BOP:NMM | Preact Time (min) | Solv. | Comp 2 | % Tyr Inc |
|---|---|---|---|---|---|---|---|
| 1 | | Tyr PFSA | — | — | Wash B | Phe PFSA | 28.0 |
| 2 | | Tyr PFSA | — | — | DMF | Phe PFSA | 23.7 |
| 3 | A | Tyr + BOP | 1:1:1 | 1 | DMF | Phe PFSA | 23.1 |
| 4 | A | Tyr + BOP | 1:1:1 | 2 | DMF | Phe PFSA | 23.6 |
| 5 | A | Tyr + BOP | 1:1:1 | 5 | DMF | Phe PFSA | 25.2 |
| 6 | A | Tyr + BOP | 1:1:1 | 10 | DMF | Phe PFSA | 26.2 |
| 7 | B | Tyr + BOP | 1:1.5:1.5 | 1 | DMF | Phe PFSA | 25.7 |
| 8 | B | Tyr + BOP | 1:1.5:1.5 | 2 | DMF | Phe PFSA | 26.8 |
| 9 | B | Tyr + BOP | 1:1.5:1.5 | 5 | DMF | Phe PFSA | 30.1 |
| 10 | B | Tyr + BOP | 1:1.5:1.5 | 10 | DMF | Phe PFSA | 34.6 |
| 11 | C | Tyr + BOP | 1:1.5:1 | 1 | DMF | Phe PFSA | 23.5 |
| 12 | C | Tyr + BOP | 1:1.5:1 | 2 | DMF | Phe PFSA | 25.9 |
| 13 | C | Tyr + BOP | 1:1.5:1 | 5 | DMF | Phe PFSA | 26.3 |
| 14 | C | Tyr + BOP | 1:1.5:1 | 10 | DMF | Phe PFSA | 29.4 |
| 12 | D | Tyr + BOP | 1:0.5:1 | 10 | DMF | Phe PFSA | 28.7 |
| 16 | D | Tyr + BOP + HOBt | 1:1:1.5 | 10 | DMF | Phe PFSA | 42.7 |

Figure 4:
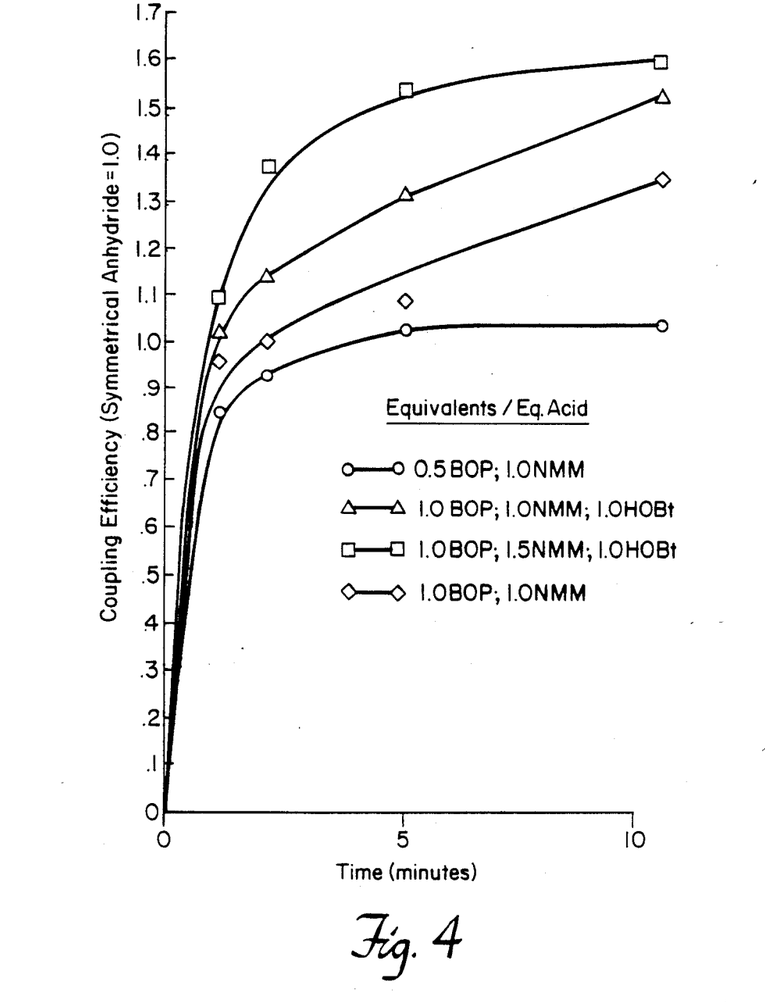
FIG. 4 is a graph illustrating BOP Reagent coupling efficiency as a function of time.

A graphic illustrating the coupling efficiency using BOP Reagent versus time as reported in TABLE II is illustrated in FIG. 4.

A ranking of the coupling efficiency of various activation methods is set forth in the following TABLE III:

TABLE III
COUPLING EFFICIENCY RANKING OF ACTIVATION METHODS FOR SOLID PHASE PEPTIDE SYNTHESIS

| | | Relative Efficiency |
|---|---|---|
| 1. | BOP + HOBt | 1.8 |
| 2. | DBTO | 1.8 |
| 3. | BOP + 10 min preactivation | 1.4 |
| 4. | Direct DIPCDI Coupling (1:1 Molar Ratio, 2 min. preactivation) | 1.33 |
| 5 & 6. | DIPCDI + Dhobt = DIPCDI + HOBt | 1.2 |
| 7 & 8. | BOP = preformed symmetrical anhydride | 1.0 |
| 9. | DIPCDI + HOPFP | 0.9 |
| 10. | Bop-Cl | 0.8 |
| 11. | IIDQ | 0.34 |
| 12 & 13. | DIPCDI + Tetrazole = DIPCDI + Benzotriazole | 0.27 |
| 14. | Bates Reagent + HOBt | 0.23 |
| 15. | EEDQ | 0.24 |
| 16. | DPPA | 0.16 |
| 17. | Bates Reagent | |
| 18. | Woodwards Reagent K | <0.05 |
| 19. | Woodwards Reagent L | |

As can be seen from the results set forth in TABLES II and III, activation with pure BOP Reagent is substantially the same as that utilizing preformed symmetrical anhydrides. Quite surprisingly, when additional HOBt is utilized with the BOP Reagent, coupling efficiency increases to 1.8 times that of the preformed symmetrical anhydride. Use of HOBt with conventional DIPCDI increases efficiently only to 1.2 times that of the preformed symmetrical anhydride.

It will thus be seen that the objects set forth above, among those made apparent from the preceding description, are efficiently attained and, since certain changes may be made in carrying out the above method and in the composition set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Particularly it is to be understood that in said claims, ingredients or compounds recited in the singular are intended to include compatible mixtures of such ingredients wherever the sense permits.

What is claimed is:

1. A method of coupling amino acids to the reactive functionality of a synthesis resin or unprotected amine group of the last amino acid residue in sold phase peptide synthesis, comprising:

reacting a protected amino acid of the formula wherein X is an amine protecting group and R is the amino acid side chain in the presence of Benzotriazolyloxytris(dimethylamino)phosphonium hexafluorophosphate (BOP Reagent) and a carboxyl group ionizer (base) and a coupling efficiency increasing amount of hydroxybenzotriazole (HOBt).

2. The method of claim 1, wherein between about 0.5 to 2.0 molar equivalents of the BOP reagent per equivalent of the protected amino acid is present.

3. The method of claim 1, wherein the protected amino acid, BOP reagent and HOBt are dissolved in a non-nucleophilic organic solvent.

4. The method of claim 3, wherein the base is selected from the group consisting of quaternary ammonium compounds and tertiary amines.

5. The method of claim 3, wherein the base is N-Methylmorpholine (NMM).

6. The method of claim 5, wherein the NMM is present in an amount between about 1.0 and 2.5 equivalents per equivalent of amino acid.

7. The method of claim 3, wherein the organic solvent is N,N-Dimethylformamide (DMF).

8. The method of claim 3, wherein between about 0.5 to 2.0 molar equivalents of the BOP reagent is present per equivalent of the protected amino acid.

9. The method of claim 6, wherein the protected amino acid BOP reagent and HOBt are dissolved in a non-nucleophilic organic solvent.

10. The method of claim 9, including between about 1.0 and 2.0 equivalents of NMM per equivalent of amino acid.

11. The method of claim 2, further including between 1.0 and 2.0 equivalents of HOBt per equivalent of amino acid.

12. The method of claim 11, wherein between about 1.0 to 1.5 equivalents of HOBt is present per equivalent of amino acids.

13. The method of claim 12, wherein the protected amino acid and BOP-HOBt Reagent are dissolved in an organic solvent.

14. The method of claim 13, further including between about 1.0 and 1.5 equivalents of NMM per equivalent of amino acid.

15. An activator for solid phase peptide synthesis comprising a mixture of BOP and HOBt.

16. The activator of claim 15, wherein between about 0.5 and 2 equivalents of BOP and between about 1.0 and 2.0 equivalent of HOBt are present per equivalent of amino acid.

* * * * *